US00PP08096P

United States Patent [19]

van der Knaap

[11] Patent Number: Plant 8,096

[45] Date of Patent: Jan. 12, 1993

[54] CHRYSANTHEMUM PLANT — TIGRIS CULTIVAR

[75] Inventor: Jacques C. M. van der Knaap, DeLier, Netherlands

[73] Assignee: Fides Beheer B.V., De Lier, Netherlands

[21] Appl. No.: 679,537

[22] Filed: Apr. 2, 1991

[51] Int. Cl.[5] ..... A01H 5/00

[52] U.S. Cl. ..... Plt./82.3

[58] Field of Search ..... Plt./74, 74.1, 82.2, Plt./82.3

[56] References Cited

U.S. PATENT DOCUMENTS

P.P. 5,064 6/1983 Shoesmith ..... Plt. 78

*Primary Examiner*—Howard J. Locker

*Attorney, Agent, or Firm*—Burns, Doane, Swecker & Mathis

[57] ABSTRACT

A new and distinct cultivar of Chrysanthemum plant named Tigris is provided. The new cultivar was the result of a controlled breeding program wherein the Klondike cultivar (U.S. Plant Pat. No. 4,978) was pollinated by an unnamed plant designated 84.815. More specifically, the new cultivar forms attractive orange flowers having a yellow-green center when immature. The inflorescence tends to be pyramidal in configuration. The response period of the flowers is approximately nine weeks. Resistance to white rust is exhibited as well as a reduction in leafminer susceptibility (i.e., partial resistance) The new cultivar is particularly suited for use in the production of a cut single spray under greenhouse conditions.

1 Drawing Sheet

SUMMARY OF THE INVENTION

The present invention comprises a new and distinct cultivar of Chrysanthemum, botanically known as *Dendranthema morifolium* Ramat., previously, *Chrysanthemum morifolium*, Ramat., and hereinafter is referred to by the cultivar name Tigris.

The new cultivar is the product of a planned breeding program which had as its objective the creation of a new Chrysanthemum cultivar which exhibits attractive orange single flowers having a green center when immature, exhibits a flower response period of approximately nine weeks, and possesses the ability to produce flowers of commercially acceptable quality throughout the year in a cut mum production program. Such combination of traits is not believed to have been present in the previously available Chrysanthemum cultivars. This objective was satisfactorily fulfilled in the cultivar of the present invention.

The breeding program which resulted in the production of the new cultivar of the present invention was carried out in a controlled environment during 1986 at De Lier, The Netherlands. The female parent (i.e., the seed parent) was the Klondike cultivar (U.S. Plant Pat. No. 4,978) and the male parent (i.e., the pollen parent) was an unnamed plant designated 84.815. The parentage of the new cultivar can be summarized as follows:

Klondike × 84.815

The seeds resulting from the above pollination were sown and plantlets were obtained which were physically and biologically different from each other. Selective study resulted in the identification of a single plant of the new variety.

It was found that the new cultivar of the present invention:

(a) exhibits attractive single flowers having an overall diameter of approximately 70 to 75 mm. wherein the ray florets are orange and the disc florets are yellow-green in coloration when immature, (b) bears flowers in a somewhat pyramidal configuration, (c) exhibits a flower response period of approximately nine weeks, (d) exhibits resistance to white rust, and (e) has the ability to produce flowers of commercially acceptable quality throughout the year in a cut mum production program.

Asexual reproduction of the new cultivar by cuttings initially taken during December, 1986, as performed at De Lier, The Netherlands, in a controlled environment has demonstrated that the characteristics of the new cultivar as herein disclosed are firmly fixed and are retained through successive generations of asexual propagation.

Tigris has not been observed under all possible environmental conditions to date. Accordingly, it is possible that the phenotype may vary somewhat with variations in the environment, such as temperature, light, day length, contact with pesticides and/or subjection to growth retardant treatments.

When the new cultivar of the present invention is compared to the Bronze Reagan cultivar (non-patented in the United States), it is observed that the overall flower size tends to be smaller, the number of petal rows is reduced, the flower response tends to be slower, resistance to white rust is present, and there is a lesser susceptibility of leafminer. Otherwise the flower type, plant vigor, and foliage tend to be substantially the same in each instance.

BRIEF DESCRIPTION OF THE PHOTOGRAPH

The accompanying photograph shows as nearly true as it is reasonably possible to make the same in a color illustration of this character, a typical specimen of an overall plant of the new cultivar. The plant was grown in a greenhouse at De Lier, The Netherlands.

DETAILED DESCRIPTION

The chart used in the identification of colors described hereafter is the R.H.S. Colour Chart of The Royal Horticultural Society, London, England. The color values were determined at 11:00 a.m. to 12:00 noon under natural daylight conditions at De Lier, The Netherlands, during October, 1990. The plants described were grown under standard greenhouse conditions which approximate those commonly utilized for the production of cut mums.

Classification:

*Botanical.*—*Dendranthema morifolium* Ramat., cv. Tigris.

*Commercial.*—Cut single spray.

Inflorescence

A. Capitulum:

*Form.*—Pyramidal.

*Type.*—Single.

*Diameter across face.*—Approximately 70 to 75 mm. on average.

B. Corolla of ray and disc florets:

*Diameter of disc.*—Approximately 15 mm. on average.

*Color* (*General tonality from a distance of three meters*).—Orange.

*Color ray florets* (*top surface*).—Greyed-Orange Group 167A.

*Color disc florets.*—Yellow-Green Group 153D when immature.

C. Reproductive organs:

*Androecium.*—Present in disc florets.

*Gynoecium.*—Present in both disc and ray florets.

Plant

A. General appearance:

*Height.*—Approximately 100 cm. on average.

Foliage:

*Color* (*upper surface*).—Yellow-Green Group 147A.

*Color* (*under surface*).—Yellow-Green Group 147C.

I claim:

1. A new and distinct cultivar of Chrysanthemum plant named Tigris, substantially as herein shown and described, which:

(a) exhibits attractive single flowers having an overall diameter of approximately 70 to 75 mm. wherein the ray florets are orange and the disc florets are yellow-green in coloration when immature, (b) bears flowers in a somewhat pyramidal configuration, (c) exhibits a flower response period of approximately nine weeks, (d) exhibits resistance to white rust, and (e) has the ability to produce flowers of commercially acceptable quality throughout the year in a cut mum production program.

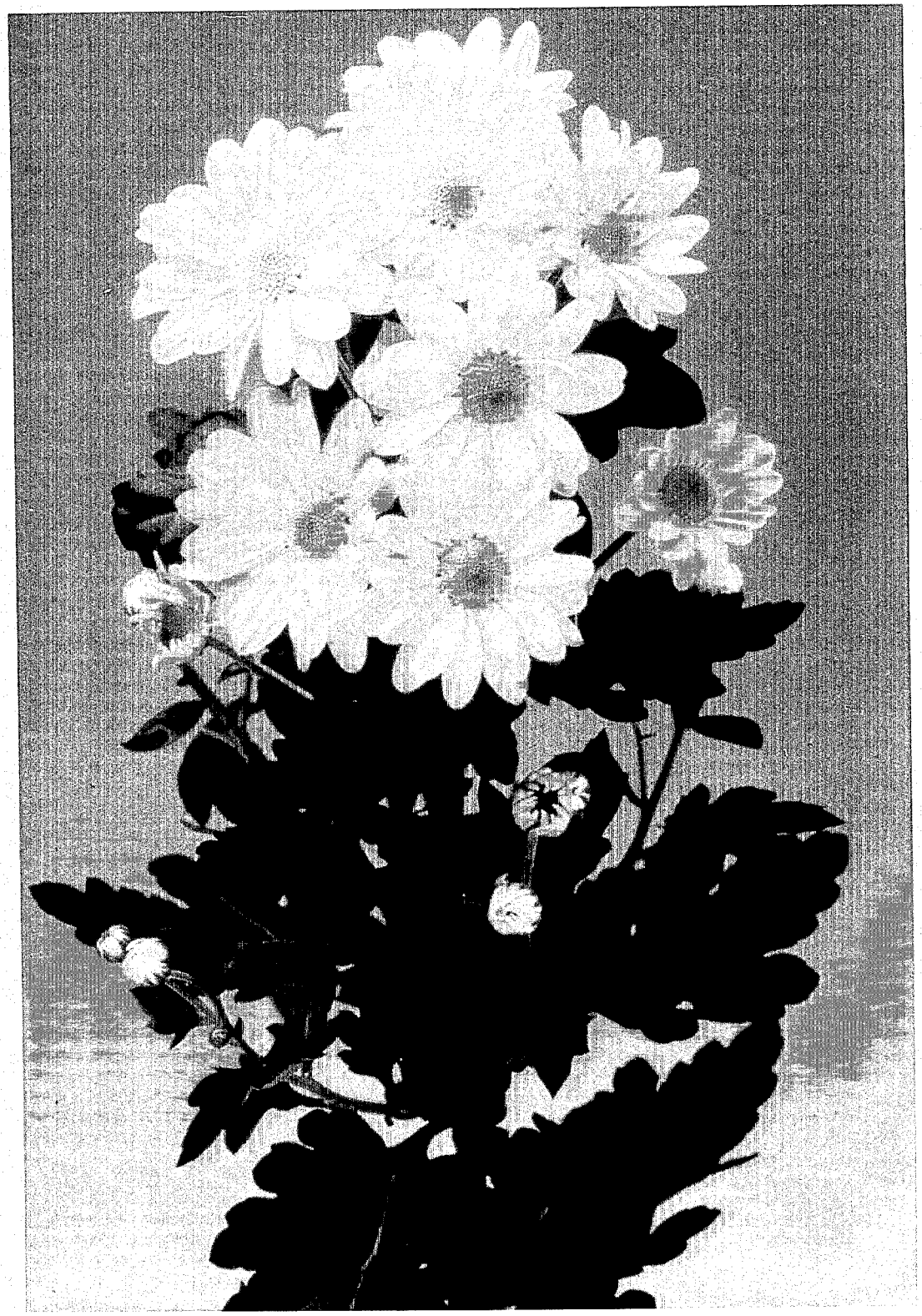

* * * * *